United States Patent [19]

Rule

[11] Patent Number: 4,776,430
[45] Date of Patent: Oct. 11, 1988

[54] CRANKCASE DRAINAGE DEVICE

[76] Inventor: Morris M. Rule, 8250 Via Paseo del Norte - Apt H102, Scottsdale, Ariz. 85258

[21] Appl. No.: 37,685

[22] Filed: Apr. 13, 1987

[51] Int. Cl.$^4$ .............................................. F16N 33/00
[52] U.S. Cl. ...................................... 184/1.5; 137/539
[58] Field of Search ..................... 184/1.5, 106, 105.1, 184/105.3; 137/539; 222/518, 496

[56] References Cited

U.S. PATENT DOCUMENTS

| | | | |
|---|---|---|---|
| 1,846,877 | 2/1932 | Knapp | 184/105.3 |
| 1,945,872 | 2/1934 | Tappe | 222/496 |
| 2,191,611 | 2/1940 | Eshbaugh | 137/539 |
| 2,206,992 | 7/1940 | Wood | 184/1.5 |
| 2,216,360 | 10/1940 | Sweetland | 184/1.5 |
| 3,282,380 | 11/1966 | Burrell et al. | 184/1.5 |
| 3,343,564 | 9/1967 | Peeples | 137/539 |
| 3,437,082 | 4/1969 | Bouwkamp | 137/539 |
| 3,725,990 | 4/1973 | Petersen | 137/539 |
| 3,743,053 | 7/1973 | Kuklewicz | 184/1.5 |
| 4,269,237 | 5/1981 | Berger | 137/539 |
| 4,347,915 | 9/1982 | Cooper | 137/539 |

FOREIGN PATENT DOCUMENTS 1502672 11/1967 France ................................ 137/539

Primary Examiner—Leonard E. Smith
Attorney, Agent, or Firm—LaValle D. Ptak

[57] ABSTRACT

A drain plug adapter for use in place of a standard drain plug in the crankcase of an internal combustion engine includes two portions. The first portion is a drain plug adapter housing having a cylindrical passage through it in which a ball check valve is mounted. The ball check valve is resiliently biased by means of a compression coil spring into engagement with a rubber O-ring mounted in an annular groove near the upper end of the drain plug adapter to form a valve seat for engagement by the ball under bias of the compression coil spring. A valve body coupler is threadedly attached to the lower end of the drain plug adapter and has a fluid path through it in communication with the passage through the drain plug adapter. The coupler is connected by means of a fluid conduit to an electric motor driven pump for withdrawal oil from the crankcase by creation of a vacuum beneath the ball of the check valve to move it downwardly to permit oil to be withdrawn.

22 Claims, 1 Drawing Sheet

CRANKCASE DRAINAGE DEVICE

BACKGROUND OF THE INVENTION

Internal combustion engines used in automobiles and trucks all employ various systems for pumping oil from a sump through various parts of the engine to lubricate the moving parts. The oil typically is located in the crankcase beneath the engine to which an oil pan or reservoir is attached. This oil becomes dirty and breaks down and must be changed at regular intervals to prolong the life of the engine.

Typical internal combustion engine crankcases have a drain plug located at the bottom of the crankcase at its lowermost point. Usually, the old oil is removed first by placing a funnel or container beneath the drain plug location. The drain plug then is removed to permit the oil to flow out of the bottom of the crankcase by gravity. After the oil has drained out of the crankcase, the plug is replaced; and new oil is poured into the engine from the top. In service stations, a waste drum typically is located on the floor beneath the point where oil is drained from the engine. This waste drum occupies a substantial space in the floor area directly beneath the engine. The drum usually is placed on wheels, so it may be moved out of the way when a vehicle which has been raised on a hoist above the drum location is lowered again to the ground. Even though this is a cumbersome procedure, it is widely used in service stations.

Many automobile and truck owners prefer to change their own oil. For such owners, a hydraulic hoist of the type used in service stations generally is not available. Consequently, a relatively shallow pan or other container is placed on the ground beneath the vehicle and the owner must slide under the vehicle to remove and replace the crankcase drain plug. This is a messy and difficult undertaking for most people. Consequently, changing the oil in motor vehicles most frequently is done in service stations, because of the availability of hoists to lift the vehicle above ground to permit removal and reinsertion of the crankcase drain plug.

Various techniques have been devised in the past for discharging oil from the crankcase without the necessity for getting beneath the vehicle to remove the typical crankcase drain plug. One such approach is disclosed in the U.S. Pat. to Sweetland No. 2,216,360. This patent is directed to a specialized crankcase which has a built in pump and discharge pipe attached for operation from above. The crankcase drain plug is permanently installed in this device. The device of Sweetland, however, requires a non-standard construction of the oil pan, so that it is not capable of simple retrofitting on existing automobiles.

Another patent which is directed to an automatic oil changer, for removing oil from the bottom of the crankcase without the necessity for removing the crankcase drain plug to accomplish the removal, is disclosed to the U.S. Pat. to Burrell No. 3,282,380. The system of Burrell has a permanently attached evacuation hose connected to the opening in the bottom of the crankcase in place of the normal drain plug. This hose then is connected to a direct current pump which may be activated to pump out the oil from the crankcase. A container is mounted in the upper portion of the engine compartment or on the engine block itself to receive the discharged oil from the pump. No valves are provided in the system to prevent oil from the crankcase to drain into the line connected from the crankcase to the pump intake. Consequently, if the line or tube connected between the crankcase drain opening and the pump should develop a leak or become dislodged, it is possible for all of the oil to drain out of the crankcase. If the engine is running when this occurs, the result could be significant damage to the engine.

Two other patents which are directed to nearly identical systems for power removal of oil from the crankcase of an automobile engine without the necessity for elevating the automobile or for removing the drain plug from the crankcase are the U.S. Pat. Nos. to Wood 2,206,992 and Kuklewicz 3,743,053. Each of these patents discloses the use of an adapter, with a ball check valve in it, which is substituted for the drain plug normally used in the bottom of the crankcase. This adapter has a discharge opening in it which is connected to an evacuation line. The evacuation line then is connected to a normally inoperative pump. When the pump is operated, however, the vacuum or suction on the line causes the check valve to open and release the oil from the crankcase. The oil then moves through the line and the pump into a discharge receptacle. Upon termination of the oil evacuation operation, the pump is turned off, the check valve returns to a closed position to close the opening in the bottom of the crankcase, and the crankcase may be refilled with fresh oil. The automobile engine then is operated in its normal manner until the next time evacuation of oil from the crankcase is desired.

The devices of both Wood and Kuklewicz provide an additional degree of protection in the event the evacuation line connected to the adapter should become loose or broken. If this should occur, the check valve will hold the drain opening closed; so that accidental discharge of the oil will not occur. These devices, however, are subject to damage inasmuch as if either of the adapters of Wood or Kuklewicz should strike an obstruction beneath a moving vehicle, the adapter could become broken away. In such an event, the spring holding the ball of the check valve would be released and the drain opening in the bottom of the crankcase no longer would be closed. Oil then could drain out without the knowledge of the vehicle operator and result in damage to the engine.

It also should be noted that the structure of the Kuklewicz check valve cannot readily be manufactured in the form disclosed in Kuklewicz. It is necessary to make the check valve portion of Kuklewicz in either two mating vertical sections or in a separate top section which would somehow be mounted onto the remainder of the body. Otherwise, the spring and ball cannot be inserted into the check valve chamber of Kuklewicz.

In Wood, additional steps are necessary to provide a valve seat for the ball check valve by rolling or peening the upper annular edge of the drainage fitting over the valve seat to hold the valve seat in place. If this is not carefully done, the valve seat may be misaligned and could permit leakage of oil past the ball as a result.

It is desirable to provide an adapter for use with standard automobile crankcases to permit the power evacuation of oil from the crankcase through an opening in its bottom, which overcomes the disadvantages of the prior art, which is reliable in operation, is inexpensive, and which provides an added degree of safety in the event the power drain components connected to it should become dislodged or broken.

SUMMARY OF THE INVENTION

It is an object of this invention to provide an improved check valve structure.

It is another object of this invention to provide an improved drain plug adapter for use in a power oil removal system.

It is an additional object of this invention to provide an improved device for removing oil from the bottom of an engine crankcase.

It is a further object of this invention to provide an improved power oil removal unit for attachment to the drain plug opening of an internal combustion engine crankcase which has improved safety characteristics to prevent undesired drainage of oil from the crankcase.

In accordance with a preferred embodiment of the invention, a check valve unit, which is particularly adapted for use in a suction drainage system for removing oil from the crankcase of an internal combustion engine, includes a drain plug adapter housing which fits into the drain plug opening of the crankcase. The adapter housing has a cylindrical passage through it, and the upper portion of the passage has a larger diameter than the lower portion. This forms a shoulder between the two portions within the adapter housing. A spring is placed in the upper portion of the passage and is supported by the shoulder. A valve member (ideally a ball valve) is supported by the second end of the spring; and a removable, resilient valve seat is placed in the upper end of the passage adjacent the top of the adapter housing.

Provision also may be made for attaching a second coupler to the lower portion of the adapter housing to be used for attachment to an evacuation line for applying a suction or partial vacuum to pull oil out of the crankcase, with the valve member collapsing the spring, to withdraw oil through the adapter housing. Upon release of the partial vacuum, the spring forces the valve member into engagement with the valve seat to close the opening.

DETAILED DESCRIPTION

Figure 1:
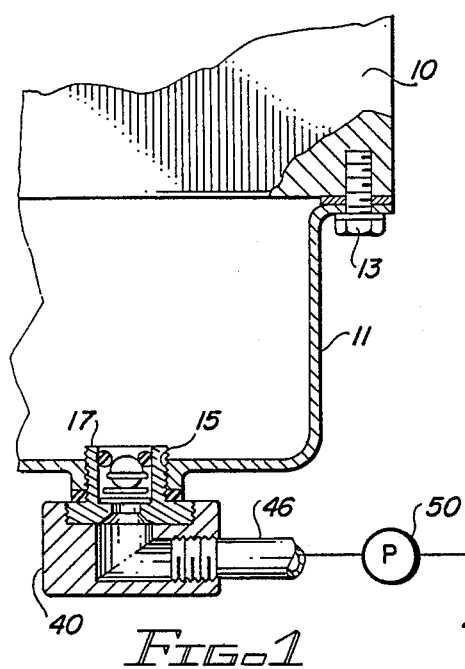
FIG. 1 is a partial sectional view of a preferred embodiment of the invention.

Reference now should be made to the drawing in which the same reference numbers are used in all three figures to designate the same or similar components. FIG. 1 illustrates a portion of a standard internal combustion engine block 10 which has a crankcase oil pan 11 attached to its lower side by means of suitable bolts 13. The engine, oil pan, and bolts may be of any standard configuration. The crankcase oil pan 11 for such an engine typically has a drain plug opening 15 in the bottom. This opening may be of different diameters for different vehicles, and it typically is an internally threaded reinforced opening in the oil pan 11 as illustrated in FIG. 1.

Figure 3:
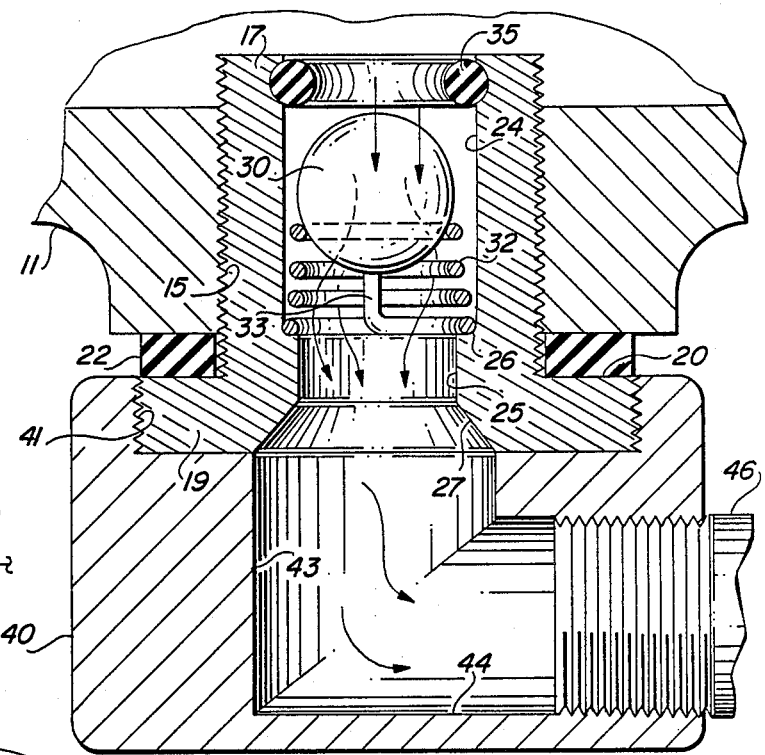
FIG. 3 is an enlarged cross-sectional view of the embodiment of FIG. 1 showing the device in a second condition of operation.
Figure 2:
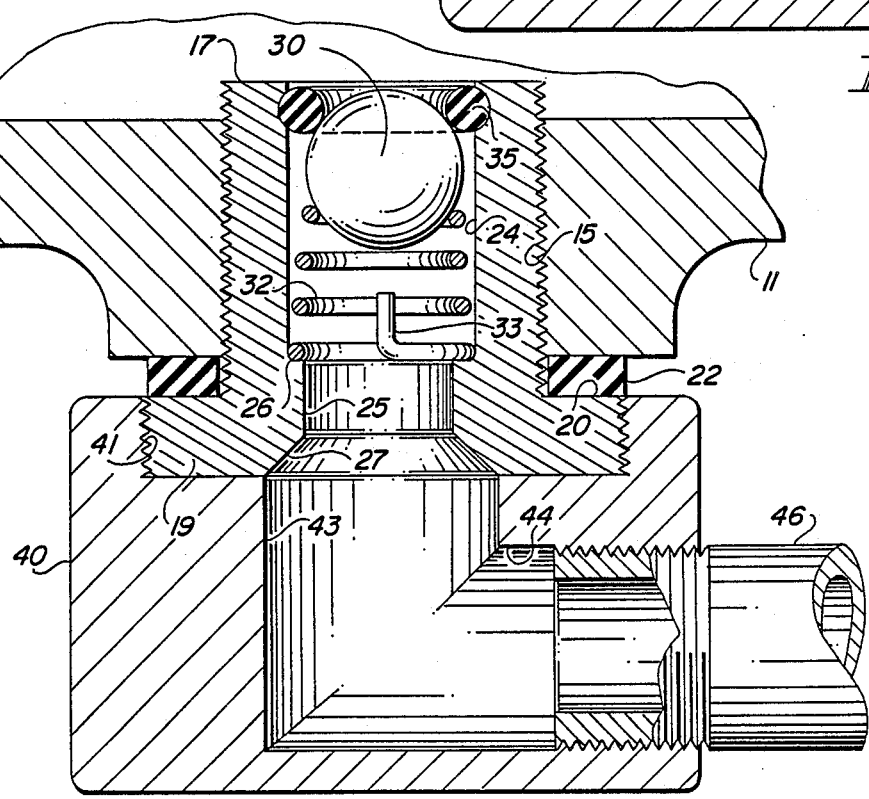
FIG. 2 is an enlarged cross-sectional viewq of portion of the device shown in FIG. 1 in one condition of operation.

In the embodiment which is shown in FIGS. 1, 2, and 3, the normal crankcase oil pan drain plug is removed and discarded. In its place, a check valve adapter 17 is threaded into the drain plug opening 15 to firmly seat a shoulder 20 of a flange 19 against a gasket or washer 22 to seal the drain plug opening.

The adapter 17 (externally threaded) has a cylindrical passageway through it, comprising an upper portion 24 and a lower portion 25 which are co-axial with one another. The upper portion 24 has a larger internal diameter than the lower portion 25, so that a shoulder 26 is formed at the junction between the two passageways. For some applications, it also may be desirable to outwardly flare the bottom end of the lower cylindrical portion 25 as indicated at 27 to provide an enlarged opening at the bottom of the adapter 17. As is clearly seen in all three figures, the passageways 24 and 25 comprise linearly aligned cylindrical passageways extending from the top through the bottom (or from a first end through a second end) of the adapter 17.

A ball check valve assembly then is placed in the upper portion 24 to normally close the passageway to prevent oil from draining through it. The check valve includes a tapered coil spring 32, the lower end of which is configured to rest on the shoulder 26. The lower end of the spring 32 terminates in an inwardly and upwardly extending portion 33 which is provided to engage the ball 30 to establish the lowermost point of travel which may be attained by the ball 30 when the ball check valve is opened. The upper end of the spring 32 is inwardly tapered to a smaller diameter than the lower end and supports a ball 30 which may be a stainless steel or nylon ball.

In construction, the spring 32 is placed in the passageway 24. Then the ball 30 is placed on top of the spring 32 and pressed downwardly. A valve seat in the form of a rubber or neoprene grommet 35 then is pressed into an annular groove near the upper end of the passageway 24. This structure is illustrated most clearly in FIG. 2.

The groove in the upper end of the passageway 34 is selected to firmly hold the grommet 35 in place, and the resiliency of the grommet assures that it is maintained in the groove in the position shown in FIGS. 2 and 3. In addition, since the grommet is made of a deformable rubber or plastic material, it functions as a secure valve seat when the ball 30 is pressed upwardly into it by means of the spring 32, as illustrated in FIG. 2.

A second part of the assembly comprises a coupler body 40 which has an annular depression formed in it with internal threads 41 to engage and be threaded on the externally threaded flange 19 as illustrated in FIG. 2. A gasket or other sealant may be used between the horizontal mating surfaces of the coupler body 40 and the bottom of the flange 19 where they abut one another, if desired.

The coupler body 40 has an "L" shaped channel through it, comprising sections 43 and 44 to provide an opening from the top of the body 40 outwardly through the right-hand side, as illustrated in FIGS. 2 and 3. The internal diameter of the portion 43 is selected to match the widest diameter of the outwardly flared passage portion 27 in the flange 19, as clearly illustrated in both FIGS. 2 and 3. The right-hand end of the passage 44 is internally threaded for engagement with an externally threaded coupler for a drain pipe 46.

When oil is to be removed from the interior of the crankcase oil pan 11, a suitable electric or vacuum pump 50 is turned on to pull oil through the pipe or conduit 46 to the right, as viewed in all three figures. When the pump 50 is turned on, a partial vacuum is created in the chambers formed by the passageways 43 and 44 in the coupler body 40 and in the passageways 27, 25, and 24 of the valve adapter plug 17. The resiliency of the spring 42 is selected such that when this vacuum is applied, the ball 30 is drawn downwardly, as shown in FIG. 3 to permit oil to be withdrawn through the now open valve from the bottom of the oil pan 11. This oil then blows and through the various passageways in the drain plug adapter 17 and the coupler body 40 out through the pipe 46. The oil which is withdrawn in this manner is disposed of in accordance with any known technique, such as disclosed in the above mentioned patents.

It is generally recommended that the oil be withdrawn from the crankcase oil pan 11 when the engine is warm. This causes all of the sludge and other contaminants in the oil will be thoroughly mixed in it and the oil is in its most fluid state. Normally, under these conditions of operation, the ball 30 is only drawn downwardly a relatively short distance, sufficient to clear the valve seat 35 and does not attain the lowermost position shown in FIG. 3. However, if the oil is very viscous (such as for heavy oil or for cold oil) it may be possible for sufficient vacuum to be built up in the pipe 46 by the pump 50 that the ball 30 is drawn down far enough to engage the spring at the shoulder 26 and close the lower passageway 25 in the valve adapter. To prevent this from happening, the up-turned end 33, described previously, is provided on the spring 32. As shown in FIG. 3, this end 33 engages the bottom of the ball 30 to establish the lowest point of travel which may be attained by the ball 30. As illustrated, this point is sufficient to permit oil and sludge to be withdrawn from the crankcase without the ball 30 closing the opening even, though a relatively strong suction or partial vacuum occurs in the pipe 46.

Typical dimensions for the various parts which are illustrated in FIGS. 2 and 3 are for the valve adapter 17 to have an exterior diameter of approximately ½". This may vary depending upon the particular automobile with which the device is used, since the drain plug openings vary somewhat from vehicle to vehicle of different manufacturers. The internal diameter of the upper passage 24 typically is 11/32", and the diameter of the passage 25 is ¼". The diameter of the passages 43 and 44 typically is selected to be ⅜". The height of the adapter 17 from the shoulder 20 on the flange 19 to the upper end is approximately ½", and the vertical height of the coupler body from the bottom to its top (as viewed in FIGS. 2 and 3) is 13/16". The resiliency of the spring 32 is selected so that the ball 30 will be drawn downwardly to open the valve at approximately 8" of vacuum. These dimensions are given for purposes of illustration only and may be varied for different applications if desired.

The structure which is shown also provides considerable safety in the event the vehicle in which the device is used should be driven over an obstruction in the road which would strike the coupler 40 with sufficient force to either break off the coupler 40 or to snap the pipe 46. Obviously, if the pipe 46 is broken, the spring 32 will hold the ball 30 in tight engagement with the valve seat grommet 35 to maintain the drain opening in the oil pan 11 closed. Similarly, if the body 40 is broken away, even taking a portion of the flange 19 with it, the shoulder 26 is located sufficiently high in the plug 17 that the spring 32 remains in place to hold the ball 30 into engagement with the valve seat 35, maintaining the valve closed. This feature is a significant safety feature which is not present in the abovementioned prior art patents.

It also should be noted, as illustrated most clearly in FIGS. 2 and 3, that the upper end of the valve adapter 17 extends slightly above the bottom of the inside of the oil pan 11. Typically, this extension is approximately ⅛" and does not result in any significant amount of residual oil remaining in the oil pan after the evacuation of the pan by the pump 50 is completed. For some applications, however, it may be desirable to have the upper end of the valve adapter flush with the inside surface of the oil pan 11. This does not change the operation of the devices.

The foregoing description of the preferred embodiment of the invention is to be considered as illustrative only and not as limiting. Various changes and modifications, which come within the scope of the invention, will occur to those skilled in the art without departing from such scope of the invention.

I claim:

1. A check valve particularly adapted for use in a suction drainage system for removing oil from the crankcase of an internal combustion engine through the drain plug opening in the bottom of such crankcase, said valve including in combination:
    adapter housing having first and second ends and having a cylindrical passage therethrough, said passage having a first portion of a first predetermined diameter extending from the first end of said housing and a second portion of second predetermined diameter less than said first predetermined diameter extending from the second end of said housing to form a shoulder means where said first and second portions of said passage meet;
    a flange on the second end of said adapter housing, said flange extending outwardly from said adapter housing and having a thickness less than the distance from the bottom of said flange to said shoulder means;
    means for securing said adapter housing in the drain plug opening of said crankcase, with said flange overlying the bottom of said crankcase surrounding the drain plug opening to position said shoulder means within the drain plug opening;
    compression spring means with first and second ends located in said first portion of said passage, with the first end of said spring means being supported by said shoulder means;
    valve means in said first portion of said passage and engaged by the second end of said compression spring means; and
    valve seat means in said passage adjacent the first end of said housing for engagement by said valve means, said compression spring means normally biasing said valve means into engagement with said valve seat means.

2. The combination according to claim 1 wherein said valve seat means comprises a resilient valve seat means.

3. The combination according to claim 2 wherein said passage has a groove about the circumference thereof near the first end thereof; and said valve seat means comprises a resilient O-ring seated in said groove.

4. The combination according to claim 1 wherein said valve means comprises a ball member.

5. The combination according to claim 4 wherein said spring means is a tapered coil spring, having a large end and a small end, the large end thereof engaging said shoulder means and the small end thereof engaging said ball member for resiliently pressing said ball member into engagement with said valve seat means.

6. The combination according to claim 5 wherein said spring means has a portion attached to the first end thereof extending into said passage toward the first end of said passage from said shoulder means to prevent said valve means from closing the first end of said passage when said valve means is moved out of engagement with said valve seat means.

7. The combination according to claim 1 wherein said spring means has a portion attached to the first end thereof extending into said passage toward the first end of said passage from said shoulder means to prevent said valve means from closing the first end of said passage when said valve means is moved out of engagement with said valve seat means.

8. The combination according to claim 7 wherein said valve seat means comprises a resilient valve seat means.

9. The combination according to claim 8 wherein said passage has a groove about the circumference thereof near the first end thereof; and said valve seat means comprises a resilient O-ring seated in said groove.

10. The combination according to claim 9 wherein said valve means comprises a ball member.

11. The combination according to claim 10 wherein said spring means is a tapered coil spring, having a large end and a small end, the large end thereof engaging said shoulder means and the small end thereof engaging said ball member for resiliently pressing said ball member into engagement with said valve seat means.

12. The combination according to claim 11 further including means for moving said ball member out of engagement with said valve seat means toward said shoulder means against the bias of said spring means.

13. The combination according to claim 12 wherein said means for moving said ball member comprises coupler means having a passage therein for fluid communication with said second portion of said passage at the second end of said housing; and pump means for withdrawing fluid from the passage in said coupler means by application of a vacuum thereto to pull said valve member toward said shoulder means.

14. The combination according to claim 13 wherein said coupler means and the second end of said adapter housing include mating threaded portions for securing said coupler means to the second end of said adapter housing.

15. A device for permitting withdrawal of oil from the crankcase of an internal combustion engine through the drain plug opening in the bottom of such crankcase, said device including in combination:
a drain plug adapter housing having first and second ends and having a cylindrical passage therethrough, said passage having a first portion of a first predetermined diameter extending from the first end of said housing and a second portion of second predetermined diameter less than said first predetermined diameter extending from the second end of said adapter housing to form a shoulder means where said first and second portions of said passage meet;
a flange on the second end of said drain plug adapter, said flange extending outwardly from said adapter and having a thickness less than the distance from the bottom of said flange to said shoulder means;
means for securing said drain plug adapter housing in the drain plug opening of said crankcase, with said flange overlying the bottom of said crankcase surrounding the drain plug opening and said shoulder means located above the bottom of the drain plug opening;
compression coil spring means, with first and second ends, located in said first portion of said passage, with the first end of said compression coil spring means being supported by said shoulder means;
a check valve member resiliently supported by the second end of said compression coil spring means in said first portion of said passage;
a valve seat member adjacent the first end of said adapter housing in said first portion of said passage for engagement by said valve member by compression of said coil spring means to normally close said passage;
a coupler attachment member removably secured to said second end of said drain plug adapter housing, said coupler member including a passage therethrough for fluid communication with said second end of said passage in said drain plug adapter; and
means for attaching a fluid withdrawal line to the passage through said coupler attachment member.

16. The combination according to claim 15 wherein said drain plug adapter housing has an annular groove in the first portion of said cylindrical passage adjacent the first end of said adapter housing; and
said valve seat member comprises a resilient O-ring seated in said annular groove.

17. The combination according to claim 15 wherein said coil spring is a tapered coil spring, having the widest portion thereof supported by said shoulder means and a narrower upper portion thereof in engagement with said valve means.

18. The combination according to claim 17 wherein said valve means is a spherical ball.

19. The combination according to claim 15 wherein said means for removably attaching said coupler means to said second end of said drain plug adapter housing comprises mating male and female threaded portions on the second end of said drain plug adapter housing and on of said coupler means, respectively.

20. The combination according to claim 19 wherein said valve means is a spherical ball.

21. The combination according to claim 20 wherein said coil spring is a tapered coil spring, having the widest portion thereof supported by said shoulder means and a narrower upper portion thereof in engagement with said valve means.

22. The combination according to claim 21 wherein said drain plug adapter housing has an annular groove in the first portion of said cylindrical passage adjacent the first end of said adapter housing; and
said valve seat member comprises a resilient O-ring seated in said annular groove.

* * * * *